(12) United States Patent
Wasserman et al.

(10) Patent No.: US 11,395,916 B2
(45) Date of Patent: Jul. 26, 2022

(54) ARRAYS FOR DELIVERING TUMOR TREATING FIELDS (TTFIELDS) WITH SELECTIVELY ADDRESSABLE SUB-ELEMENTS

(71) Applicant: Novocure GmbH, Root (CH)

(72) Inventors: Yoram Wasserman, Haifa (IL); Michael Krinitsky, Beer Sheva (IL); Sergey Kirilov, Shima (IL); Michael Shtotland, Beer Sheva (IL); Victor Kaikov, Atlit (IL)

(73) Assignee: Novocure GmbH, Root (CH)

( * ) Notice: Subject to any disclaimer, the term of this patent is extended or adjusted under 35 U.S.C. 154(b) by 36 days.

(21) Appl. No.: 16/686,918

(22) Filed: Nov. 18, 2019

(65) Prior Publication Data

US 2020/0155835 A1    May 21, 2020

Related U.S. Application Data

(60) Provisional application No. 62/769,319, filed on Nov. 19, 2018.

(51) Int. Cl.
*A61N 1/40* (2006.01)
*A61N 1/08* (2006.01)
*A61N 1/04* (2006.01)

(52) U.S. Cl.
CPC ............. *A61N 1/08* (2013.01); *A61N 1/0404* (2013.01); *A61N 1/40* (2013.01)

(58) Field of Classification Search
CPC .... A61N 1/08; A61N 1/3603; A61N 1/36025; A61N 1/36002; A61N 1/0529;
(Continued)

(56) References Cited

U.S. PATENT DOCUMENTS 5,938,597 A    8/1999   Stratbucker
5,974,344 A    10/1999  Shoemaker
(Continued)

FOREIGN PATENT DOCUMENTS

CN    107281635 A    10/2017
WO    2002047565 A2   6/2002
(Continued)

OTHER PUBLICATIONS

International Search Report and Written Opinion issued in application No. PCT/IB2019/059895 dated Feb. 19, 2020.
(Continued)

*Primary Examiner* — Carl H Layno
*Assistant Examiner* — Anh-Khoa N Dinh
(74) *Attorney, Agent, or Firm* — Potomac Law Group, PLLC

(57) ABSTRACT

Tumor treating fields (TTFields) can be delivered to a subject's body at higher field strengths by switching off one or more electrode elements that are overheating without switching off other electrode elements that are not overheating. This may be accomplished using a plurality of temperature sensors, with each of the temperature sensors positioned to sense the temperature at a respective electrode element; and a plurality of electrically controlled switches, each of which is wired to switch the current to an individual electrode element on or off. A controller input signals from the temperature sensors to determine the temperature at each of the electrode elements, and controls the state of the control input of each of the electrically controlled switches to selectively switch off the current or adjusted the duty cycle at any electrode element that is overheating.

20 Claims, 6 Drawing Sheets

(58) Field of Classification Search
CPC .............. A61N 1/0476; A61N 1/0456; A61N 1/0404; A61N 1/40; A61N 1/36003; A61N 1/36007; A61N 1/3601; A61N 1/36014; A61N 1/36017; A61N 1/36021
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,675,460 B2 | 6/2020 | Travers et al. |
| 10,779,875 B2 | 9/2020 | Palti et al. |
| 10,821,283 B2 | 11/2020 | Giladi et al. |
| 2004/0122500 A1 | 6/2004 | Rouns |
| 2005/0222646 A1 | 10/2005 | Kroll et al. |
| 2006/0167499 A1 | 7/2006 | Palti |
| 2007/0093788 A1 | 4/2007 | Carter |
| 2007/0225766 A1 | 9/2007 | Palti |
| 2007/0239213 A1 | 10/2007 | Palti |
| 2009/0076366 A1 | 3/2009 | Palti |
| 2010/0204560 A1 | 8/2010 | Salahieh et al. |
| 2011/0137229 A1* | 6/2011 | Palti .......... A61N 1/40 604/20 |
| 2012/0283726 A1 | 11/2012 | Palti |
| 2016/0346530 A1 | 12/2016 | Jeffery et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0085575 A1 | 3/2018 | Travers et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1† | 4/2019 | Travers |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2021/0177492 A1 | 6/2021 | Travers et al. |

FOREIGN PATENT DOCUMENTS

| | | |
|---|---|---|
| WO | 2003002185 A2 | 1/2003 |
| WO | 2016014264 A1 | 1/2016 |
| WO | 2017141257 A1 | 8/2017 |

OTHER PUBLICATIONS

Bomzon et al., "Using computational phantoms to improve the delivery of Tumor Treating Fields (TTFields) to patients," 38th Annual International Conference of the IEEE Engineering in Medicine and Biology Society (EMBC), IEEE, pp. 6461-6464, 2016.

Korshoej et al., "Enhancing Predicted Efficacy of Tumor Treating Fields Therapy of Glioblastoma Using Targeted Surgical Craniectomy: A Computer Modeling Study," Plos One, vol. 11, No. 10, p. e0164051, Oct. 2016.

Miranda et al., "Predicting the electric field distribution in the brain for the treatment of glioblastoma," Physics in Medicine & Biology, vol. 59, pp. 4137-4147, Jul. 2014.

\* cited by examiner
† cited by third party

ARRAYS FOR DELIVERING TUMOR TREATING FIELDS (TTFIELDS) WITH SELECTIVELY ADDRESSABLE SUB-ELEMENTS

BACKGROUND

TTFields therapy is a proven approach for treating tumors. FIG. 1 is a schematic representation of the prior art Optune® system for delivering TTFields. The TTFields are delivered to patients via four transducer arrays 21-24 that are placed on the patient's skin in close proximity to a tumor (e.g., as depicted in FIGS. 2A-2D for a person with glioblastoma). The transducer arrays 21-24 are arranged in two pairs, and each transducer array is connected via a multi-wire cable to an AC signal generator 20. The AC signal generator (a) sends an AC current through one pair of arrays 21, 22 during a first period of time, which induces an electric field with a first direction through the tumor; then (b) sends an AC current through the other pair of arrays 23, 24 during a second period of time, which induces an electric field with a second direction through the tumor; then repeats steps (a) and (b) for the duration of the treatment.

Each transducer array 21-24 is configured as a set of capacitively coupled electrode elements E (e.g., a set of 9 electrode elements, each of which is about 2 cm in diameter) that are interconnected via flex wires. Each electrode element includes a ceramic disk that is sandwiched between a layer of an electrically conductive medical gel and an adhesive tape. When placing the arrays on the patient, the medical gel adheres to the contours of the patient's skin and ensures good electric contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41° C. The temperature measurements on the patient's skin are obtained using thermistors T placed beneath some of the disks of the transducer arrays. In the existing Optune® system, each array includes 8 thermistors, with one thermistor positioned beneath a respective disk in the array. (Note that most arrays include more than 8 disks, in which case the temperature measurements are only performed beneath a sub-set of the disks within the array).

The AC signal generator 20 obtains temperature measurements from all 32 thermistors (4 arrays×8 thermistors per array). The controller in the AC signal generator uses the temperature measurements to control the current to be delivered via each pair of arrays in order to maintain temperatures below 41° C. on the patient's skin. The current itself is delivered to each array via an additional wire (i.e., one wire 28 for each of the arrays 21-24) that runs from the AC signal generator 20 to each array.

SUMMARY OF THE INVENTION

One aspect of the invention is directed to a first apparatus for applying an alternating electric field to a subject's body. The first apparatus comprises a plurality of capacitively coupled electrode elements, each of the electrode elements having a dielectric layer; and a support configured to hold the plurality of electrode elements so that the dielectric layer of the electrode elements can be positioned in contact with the subject's body. The first apparatus also comprises a plurality of temperature sensors. Each of the temperature sensors is positioned to sense a temperature at a respective electrode element and generate a respective signal indicative of the sensed temperature. The first apparatus also comprises an electrical conductor; and a plurality of electrically controlled switches. Each of the switches is configured to, depending on a state of a respective control input, either (a) allow current to flow between the electrical conductor and a respective electrode element or (b) prevent current from flowing between the electrical conductor and the respective electrode element. The first apparatus also comprises a controller configured to control the state of the control input of each of the switches.

In some embodiments of the first apparatus, the controller is further configured to accept, from each of the temperature sensors, the respective signal indicative of the sensed temperature; determine, based on the accepted signals, a duty cycle at which a given electrode element should be driven; and periodically toggle the state of the control input of a switch that corresponds to the given electrode element at the determined duty cycle in order to periodically prevent current from flowing between the electrical conductor and the given electrode element.

In some embodiments of the first apparatus, the controller is further configured to accept, from each of the temperature sensors, the respective signal indicative of the sensed temperature; determine, based on the accepted signals, whether a temperature at each of the electrode elements exceeds an upper threshold; and if it has been determined that a temperature at a given electrode element exceeds the upper threshold, control the state of the control input of the respective switch to prevent current from flowing between the electrical conductor and the given electrode element. Optionally, in these embodiments, the controller may be further configured to, after controlling the state of the control input to a given switch to prevent current from flowing between the electrical conductor and a respective electrode element; determine, based on the accepted signal from the respective temperature sensor whether a temperature at the respective electrode element has dropped below a lower threshold; and subsequently control the state of the control input to the given switch to allow current to flow between the electrical conductor and the respective electrode element.

In some embodiments of the first apparatus, the controller is further configured to accept the signal from each of the temperature sensors; transmit data describing the temperature at each of the temperature sensors to a second controller; receive data from the second controller indicating which of the switches should be turned off; and control the state of the control inputs of the plurality of switches based on the data received from the second controller.

In some embodiments of the first apparatus, the plurality of capacitively coupled electrode elements comprises at least 9 capacitively coupled electrode elements. In some embodiments of the first apparatus, each of the capacitively coupled electrode elements comprises a conductive plate with a flat face, and the dielectric layer is disposed on the flat face of the conductive plate. In some embodiments of the first apparatus, the support comprises a layer of foam. In some embodiments of the first apparatus, the electrical conductor comprises a trace on a flex circuit.

In some embodiments of the first apparatus, the support is configured to hold the plurality of electrode elements against an external surface of the subject's body, with the dielectric layer of the electrode elements facing the subject's body. In some embodiments of the first apparatus, the plurality of electrically controlled switches and the controller are positioned on a module that is attached to the support via a multi-conductor connector.

Another aspect of the invention is directed to a second apparatus for applying an alternating electric field to a subject's body. The second apparatus comprises a plurality of capacitively coupled sets of at least two electrode elements, each of the electrode elements having a dielectric layer; and a support configured to hold the plurality of sets of electrode elements so that the dielectric layer of the electrode elements can be positioned in contact with the subject's body. The second apparatus also comprises a plurality of temperature sensors. Each of the temperature sensors is positioned to sense a temperature at a respective set of electrode elements and generate a respective signal indicative of the sensed temperature. The second apparatus also comprises an electrical conductor; and a plurality of electrically controlled switches. Each of the switches is configured to, depending on a state of a respective control input, either (a) allow current to flow between the electrical conductor and a respective electrode element or (b) prevent current from flowing between the electrical conductor and the respective electrode element. The second apparatus also comprises a controller configured to control the state of the control input of each of the switches.

In some embodiments of the second apparatus, all of the electrode elements within any given set of electrode elements are arranged concentrically.

In some embodiments of the second apparatus, the controller is further configured to accept, from each of the temperature sensors, the respective signal indicative of the sensed temperature; determine, based on the accepted signals, a duty cycle at which a given electrode element should be driven; and periodically toggle the state of the control input of a switch that corresponds to the given electrode element at the determined duty cycle in order to periodically prevent current from flowing between the electrical conductor and the given electrode element.

In some embodiments of the second apparatus, the controller is further configured to accept, from each of the temperature sensors, the respective signal indicative of the sensed temperature; determine, based on the accepted signals, whether a temperature at each set of electrode elements exceeds an upper threshold; and if it has been determined that a temperature at a given set of electrode elements exceeds the upper threshold, control the state of the control input of at least one respective switch to prevent current from flowing between the electrical conductor and at least one of the electrode elements in the given set of electrode elements.

In some embodiments of the second apparatus, the controller is further configured to accept the signal from each of the temperature sensors; transmit data describing the temperature at each of the temperature sensors to a second controller; receive data from the second controller indicating which of the switches should be turned off; and control the state of the control inputs of the plurality of switches based on the data received from the second controller.

In some embodiments of the second apparatus, the support is configured to hold the plurality of sets of electrode elements against an external surface of the subject's body, with the dielectric layer of the electrode elements facing the subject's body. In some embodiments of the second apparatus, the plurality of electrically controlled switches and the controller are positioned on a module that is attached to the support via a multi-conductor connector.

Another aspect of the invention is directed to a third apparatus for applying an alternating electric field to a subject's body. The third apparatus comprises a plurality of first electrode elements; and a flexible support configured to hold the plurality of first electrode elements against a subject's body. The third apparatus also comprises a plurality of temperature sensors. Each of the temperature sensors is positioned to sense a temperature at a respective first electrode element and generate a respective signal indicative of the sensed temperature. The third apparatus also comprises an electrical conductor; and a plurality of electrically controlled first switches. Each of the first switches is wired in series with a respective first electrode element in a circuit that begins at the electrical conductor and ends at the respective first electrode element, and each of the first switches is configured to switch on or off independently of other first switches based on a state of a respective control input. The third apparatus also comprises a controller configured to generate an output that determines the state of the control input for each of the first switches.

In some embodiments of the third apparatus, each of the first electrode elements comprises a capacitively coupled electrode element having a dielectric layer, and the flexible support is configured to hold the plurality of first electrode elements against a subject's body with the dielectric layer of the first electrode elements facing the subject's body.

Some embodiments of the third apparatus further comprise a plurality of second electrode elements, wherein each of the second electrode elements is positioned adjacent to a respective first electrode element; and a plurality of electrically controlled second switches. Each of the second switches is wired in series with a respective second electrode element in a circuit that begins at the electrical conductor and ends at the respective second electrode element, and each of the second switches is configured to switch on or off independently of other second switches based on a state of a respective control input. The support is configured to hold the plurality of second electrode elements against the subject's body. And the controller is further configured to generate an output that determines the state of the control input for each of the second switches.

Optionally, in these embodiments, each of the first electrode elements comprises a capacitively coupled electrode element having a dielectric layer; and each of the second electrode elements comprises a capacitively coupled electrode element having a dielectric layer; and the support is configured to (a) hold the plurality of first electrode elements against a subject's body with the dielectric layer of the first electrode elements facing the subject's body, and (b) hold the plurality of second electrode elements against a subject's body with the dielectric layer of the second electrode elements facing the subject's body.

Optionally, in these embodiments, each of the second electrode elements is concentric with the adjacent respective first electrode element.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
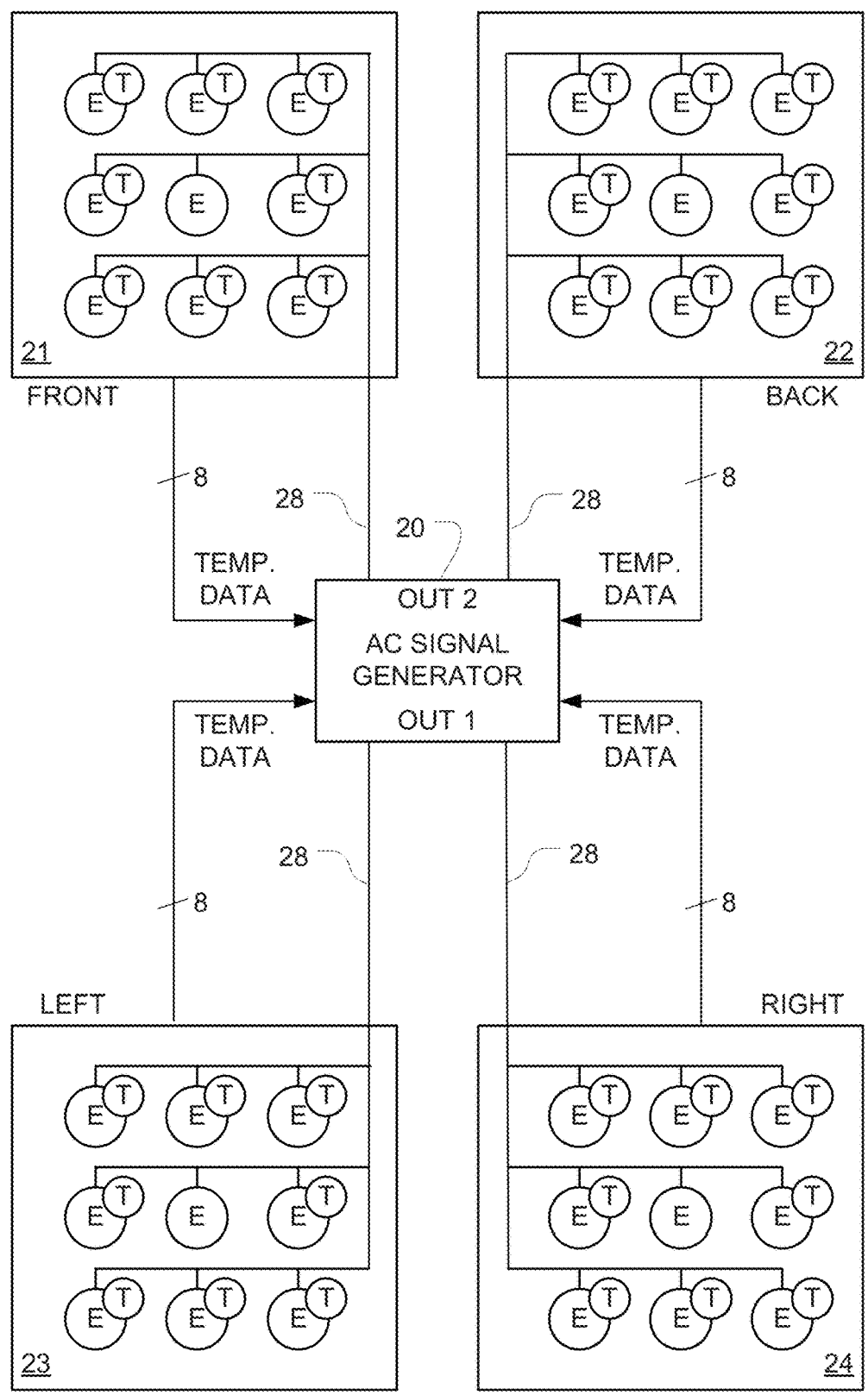
FIG. 1 is a schematic representation of the prior art Optune® system for delivering TTFields.
Figure 2A:
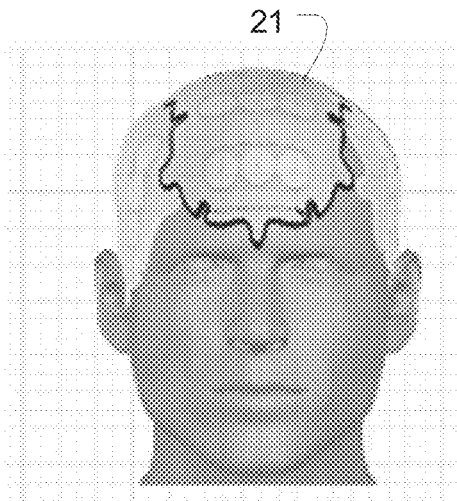
FIGS. 2A-2D depicts the positioning of transducer arrays on a person's head for treating a brain tumor.
Figure 2B:
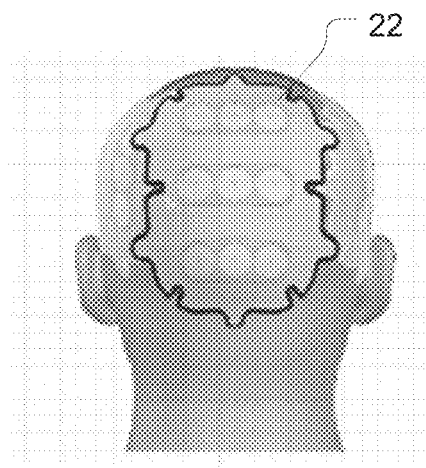
Figure 2C:
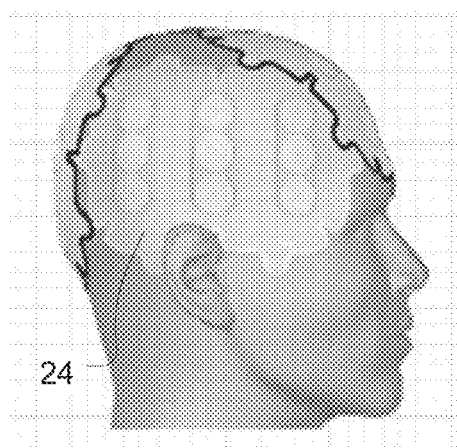
Figure 2D:
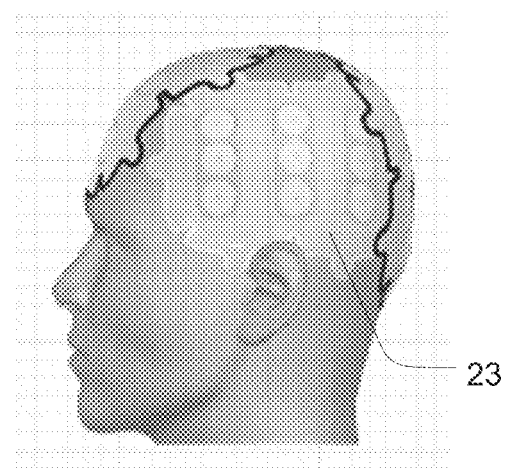

Although the prior art approach described above in connection with FIG. 1 is very effective for delivering TTFields to a tumor, the effectiveness of the treatment will drop if good electrical contact is not maintained between each of the elements in the four transducer arrays 21-24 and the person's body. This can happen, for example, if the hydrogel beneath one or more elements of the transducer arrays dries out over time, or due to hair growth beneath one or more of the elements.

Assume, for example, in a prior art system with 9 electrode elements E in each of the transducer arrays 21-24, that the hydrogel beneath a single electrode element E on the front transducer array 21 has dried out; and that enough hydrogel is present beneath (a) all the other electrode elements E of that transducer array 21, and (b) all the electrode elements E of the other transducer arrays 22-24. In this situation, the resistance between the single electrode element E and the person's body will be higher than the resistance between any of the other electrode elements and the person's body. And this increase in resistance will cause the temperature of the single electrode element E to rise more than the other electrode elements.

In this situation, the prior art AC signal generator 20 must limit the current that is applied to the front/back pair of transducer arrays 21, 22 in order to keep the temperature of the single electrode element E on the front array 21 below 41°, even though the temperature at all the remaining electrode elements E on the front and back transducer arrays 21, 22 may be well below 41° C. And this decrease in current causes a corresponding decrease in the strength of the electric field at the tumor.

The embodiments described herein can be used to minimize or eliminate the decrease in current that is coupled into the person's body, and thereby minimize or eliminate the decrease in strength of the electric field at the tumor. This may be accomplished by alternately switching the current on and off for each individual electrode element that begins to approach 41° in order to reduce the average current for those electrode elements, without affecting the current that passes through the remaining electrode elements (which are not approaching 41°).

Assume, for example, a situation in which 500 mA of current is passing through a transducer array that includes 10 electrode elements, and only a single one of those electrode elements begins to approach 41°. Assume further that a 10% reduction of current through the single electrode element would be necessary to keep the temperature at that single electrode element below 41°. Instead of achieving this 10% reduction in current by cutting the current through the entire transducer array from 500 mA to 450 mA (as in the prior art), the embodiments described herein can cut the average current through the single electrode element by 10% by switching the current through that single electrode element on and off with a 90% duty cycle, while leaving the current on full-time for all the remaining electrode elements. Note that the switching rate must be sufficiently fast so that the instantaneous temperature at the single electrode element never exceeds 41°, in view of the thermal inertia of the electrode elements. For example, a 90% duty cycle could be achieved by switching the current on for 90 ms and switching the current off for 10 ms. In some preferred embodiments, the period of switching the current on and off is less than 1 s.

When this approach is used, the current through the remaining 9 electrode elements can remain unchanged (i.e., 50 mA per electrode element), and only the current through the single electrode element is reduced to an average of 45 mA. The average net total current through the transducer array will then be 495 mA (i.e., 9×50+45), which means that significantly more current can be coupled into the person's body without exceeding 41° at any of the electrode elements.

The system may even be configured to increase the current through the remaining nine electrode elements in order to compensate for the reduction in current through the single electrode element. For example, the current through the remaining nine electrode elements could be increased to 50.5 mA per electrode element (e.g., by sending a request to the AC voltage generator to increase the voltage by 1%). If this solution is implemented, the average net total current through the entire transducer array would be (9 electrodes×50.5 mA+1 electrode×50.5 mA×0.9 duty cycle)=499.95 mA, which is extremely close to the original 500 mA of current.

If, at some subsequent time (or even at the same time), the temperature at a second electrode element begins to approach 41°, a similar technique (i.e. a reduction in the duty cycle from 100% to something less than 100%) may be used to prevent the temperature at the second electrode element from exceeding 41°.

In some embodiments, this technique may be used to individually customize the duty cycle at each of the electrode elements in order to maximize the current that flows through each of those electrode elements while keeping the temperature at each of those elements below 41°. Optionally, instead of taking remedial action to reduce the duty cycle only when the temperature at a given electrode element begins to approach 41°, the system may be configured to proactively set the duty cycle at each of the electrode elements in a given transducer array individually so as to equalize the temperature across all of the electrode elements in the array. For example, the system could be configured to individually set the duty cycle at each electrode element so as to maintain a temperature that hovers around 40.5° at each of the electrode elements. Optionally, the system may be configured to send a request to the AC voltage generator to increase or decrease the voltage as required in order to achieve this result.

This approach can be used to ensure that each and every electrode element will carry the maximum average current possible (without exceeding 41°), which will provide an increased field strength in the tumor and a corresponding improvement in the treatment.

Figure 3:
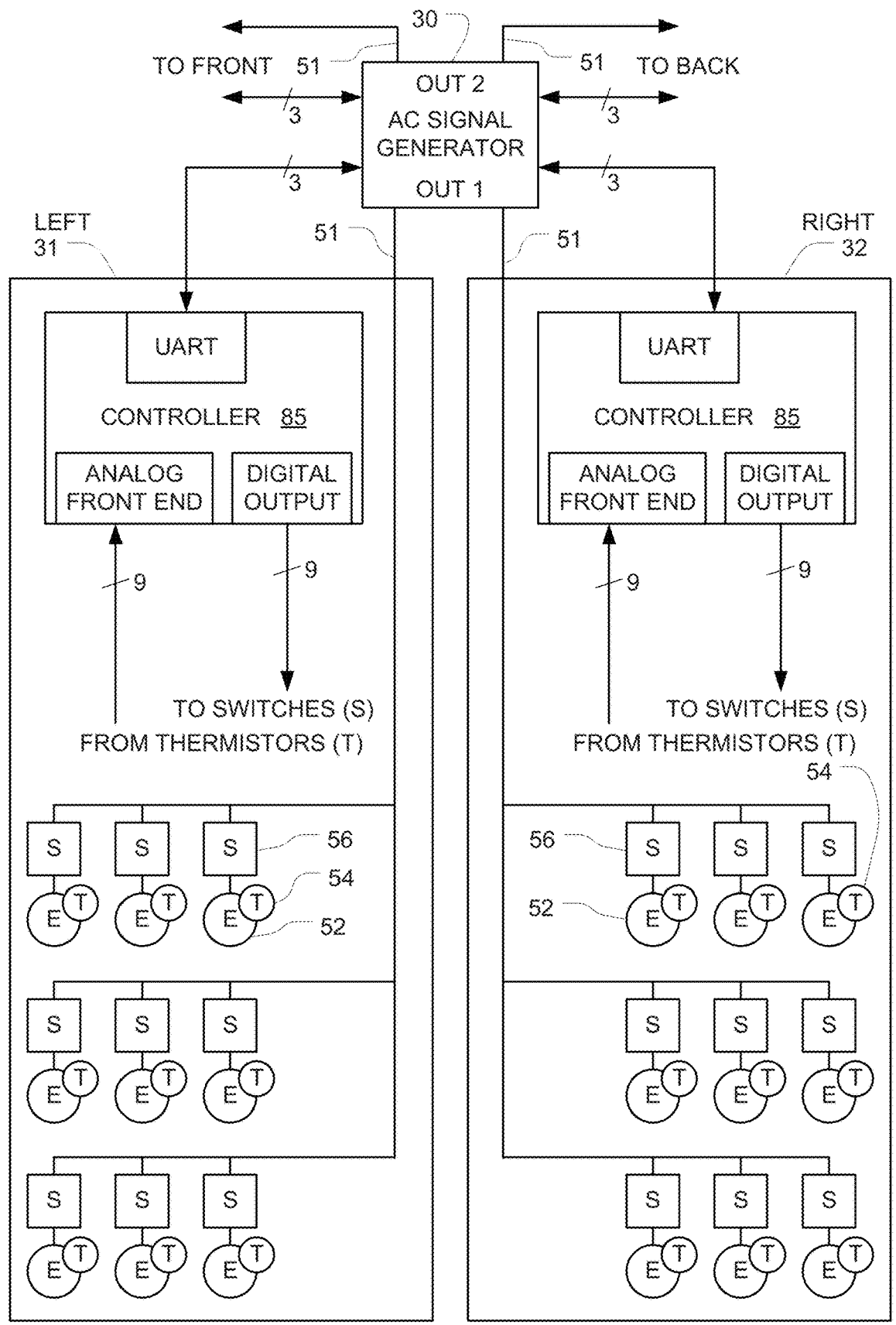
FIG. 3 depicts a first embodiment that can switch the current to each individual electrode element on or off based on the state of a set of electrically controlled switches.

FIG. 3 depicts a first embodiment that periodically switches the current on and off for each individual electrode element that begins to approach 41°. The AC signal generator 30 has two outputs (OUT1 and OUT2), each of which has two terminals. The AC signal generator 30 generates an AC signal (e.g. a 200 kHz sine wave) between the two terminals of each of those outputs in an alternating sequence (e.g., activating OUT1 for 1 sec., then activating OUT2 for one sec., in an alternating sequence). A pair of conductors 51 are connected to the two terminals of OUT1, and each of those conductors 51 goes to a respective one of the left and right transducer assemblies 31, 32. A second pair of conductors 51 are connected to the two terminals of OUT2 and each of those conductors 51 goes to a respective one of the front and back transducer assemblies (not shown). The construction and operation of the front and back transducer assemblies is similar to the construction of the left and right transducer assemblies 31, 32 depicted in FIG. 3.

Each of the transducer assemblies 31, 32 includes a plurality of electrode elements 52. In some preferred embodiments, each of these electrode elements 52 is a capacitively coupled electrode element that is similar to the prior art electrode elements used in the Optune® system. However, in this FIG. 3 embodiment, instead of wiring all of the electrode elements 52 in parallel, an electrically controlled switch (S) 56 is wired in series with each electrode element (E) 52, and all of these S+E combinations 56+52 are wired in parallel. Each of the switches 56 is configured to switch on or off independently of other switches based on a state of a respective control input that arrives from the digital output of the respective controller 85. When a given one of the switches 56 is on (in response to a first state of the respective control input), current can flow between the electrical conductor 51 and the respective electrode element 52. Conversely, when a given one of the switches 56 is off (in response to a second state of the respective control input), current cannot flow between the electrical conductor 51 and the respective electrode element 52.

In some preferred embodiments, each of the capacitively coupled electrode elements 52 is disc-shaped (e.g., with a 2 cm diameter) and has a dielectric layer on one side. The transducer assembly 31, 32 holds the electrode elements 52 against the subject's body with the dielectric layer of the electrode elements facing the subject body. Preferably, a layer of hydrogel is disposed between the dielectric layer of the electrode elements and the subject's body when the transducer assembly 31, 32 is placed against the subject's body so it can hold the electrode elements 52 against a subject's body.

In some preferred embodiments, each of the capacitively coupled electrode elements 52 comprises a conductive plate with a flat face, and the dielectric layer is disposed on the flat face of the conductive plate. In some preferred embodiments, all of the capacitively coupled electrode elements are held in place by a support structure. Optionally, this support structure may comprise a layer of foam. In some preferred embodiments, the electrical connection to each of the electrode elements 52 comprises a trace on a flex circuit.

Each of the transducer assemblies 31, 32 also includes a temperature sensor 54 (e.g., a thermistor) positioned at each of the electrode elements 52 so that each temperature sensor 54 can sense the temperature of a respective electrode element 52. Each of the temperature sensors 54 generates a signal indicative of the temperature at (e.g., beneath) the respective electrode element 52. The signals from the temperature sensors 54 are provided to the analog front and of the respective controller 85.

In embodiments where thermistors are used as the temperature sensors 54, temperature readings may be obtained by routing a known current through each thermistor and measuring the voltage that appears across each thermistor. In some embodiments, thermistor-based temperature measurements may be implemented using a bidirectional analog multiplexer to select each of the thermistors in turn, with a current source that generates a known current (e.g., 150 µA) positioned behind the multiplexer, so that the known current will be routed into whichever thermistor is selected by the analog multiplexer at any given instant. The known current will cause a voltage to appear across the selected thermistor, and the temperature of the selected thermistor can be determined by measuring this voltage. The controller 85 runs a program that selects each of the thermistors in turn and measures the voltage that appears across each of the thermistors (which is indicative of the temperature at the selected thermistor) in turn. An example of suitable hardware and procedures that may be used to obtain temperature readings from each of the thermistors is described in US 2018/0050200, which is incorporated herein by reference in its entirety.

In some preferred embodiments, the controller 85 may be implemented using a single-chip microcontroller or Programmable System on Chip (PSoC) with a built in analog front end and multiplexer. Suitable part numbers for this purpose include the CY8C4124LQI-443. In alternative embodiments, other microcontrollers may be used with either built-in or discrete analog front ends and multiplexers, as will be apparent to persons skilled in the relevant arts.

In alternative embodiments, not shown, an alternative approach (e.g., the conventional voltage divider approach) for interfacing with the thermistors may be used in place of the constant current approach described above. In other alternative embodiments, a different type of temperature sensor may be used in place of the thermistors described above. Examples include thermocouples, RTDs, and integrated circuit temperature sensors such as the Analog Devices AD590 and the Texas Instruments LM135. Of course, when any of these alternative temperature sensors is used, appropriate modifications to the circuit (which will be apparent to persons skilled in the relevant arts) will be required.

In some embodiments, the controller 85 is programmed to keep the temperature at all of the electrode elements below a safety threshold (e.g., below 41° C.) using intelligence that is built into each transducer assembly 31. This may be accomplished, for example, by programming the controller 85 to start out by setting its digital output so that each of the switches 56 is continuously on (i.e., with a 100% duty cycle). Then, based on signals arriving via the controller 85 analog front end, the controller 85 determines whether the temperature at each of the electrode elements exceeds an upper threshold (e.g. 40° C.) that is below the safety threshold. When the controller 85 detects this condition, the controller 85 reduces the duty cycle for the corresponding switch 56 by toggling the corresponding digital output at the desired duty cycle. This will interrupt the current to the corresponding electrode element 52 at the same duty cycle, thereby reducing the average current at the specific electrode elements 52 whose temperature exceeds that upper threshold. The level of reduction in current is determined by the duty cycle. For example, using a 50% duty cycle will cut the current by half; and using a 75% duty cycle will cut the current by 25%.

Notably, this procedure only interrupts the current to specific ones of the electrode elements 52 on the transducer assembly 31, and does not interrupt the current to the remaining electrode elements 52 on that transducer assembly 31. This provides a very significant advantage over the prior art, because it eliminates or reduces the need to cut the current that is being routed through the electrode elements when only a small number of those electrode elements are getting hot.

A numeric example will be useful to illustrate this point. Assume, in the FIG. 3 embodiment, that the left and right transducer assemblies 31, 32 are positioned on the left and right sides of a subject's head, respectively; that all of the switches 56 in the transducer assemblies 31, 32 are in the ON state with a 100% duty cycle; and that the AC signal generator 30 is initially outputting 500 mA of current into the conductors 51. An AC voltage will appear between the electrode elements 52 of the left transducer assembly 31 and the electrode elements 52 of the right transducer assembly 32, and the 500 mA AC current will be capacitively coupled through the electrode elements 52 through the subject's head. The controller 85 in each of the transducer assemblies 31, 32 monitors the temperature at each of the electrode elements 52 in that transducer assembly by inputting signals from each of the temperature sensors 54 via the analog front end of the controller 85. Now assume that the temperature at a given one of the electrode elements 52 in the transducer assembly 31 has risen to 40° C. This condition will be reported to the controller 85 in the transducer assembly 31 via a signal from the corresponding temperature sensor 54. When the controller 85 recognizes that the temperature of the given electrode element 52 has risen to 40° C., the controller 85 will toggle the control signal that goes to the corresponding switch 56 at the desired duty cycle in order to periodically interrupt the current to the given electrode element 52 and maintain a lower average current.

This stands in sharp contrast with the prior art devices which had to decrease the current that flows through ALL of the electrode elements as soon as the temperature at even a single one of the electrode elements 52 approached 41° C.

Note that if the duty cycle at only one of the remaining electrode elements 52 is being reduced, it may be possible to maintain the original 500 mA current (and enjoy the advantages that arise from using the full current). However, if the duty cycle at a large enough number of the electrode elements 52 is being reduced, the original 500 mA current may have to be dropped. To accomplish this, the controller 85 can send a request to the AC signal generator 30 via the UART in the controller 85. When the AC signal generator 30 receives this request, the AC signal generator 30 will reduce the output current at its corresponding output OUT1.

Optionally, the duty cycle that is selected by the controller 85 may be controlled based on the speed at which the given electrode element 52 heats up after current is applied to the given electrode element 52 (as measured via the temperature sensors 54 and the analog front end of the controller 85). More specifically, if the controller 85 recognizes that a given electrode element 52 is heating up twice as fast as expected, the controller 85 can select a duty cycle of 50% for that electrode element. Similarly, if the controller 85 recognizes that a given electrode element 52 is heating up 10% faster than expected, the controller 85 can select a duty cycle of 90% for that electrode element.

In other embodiments, instead of deterministically cutting the average current by reducing the duty cycle, the controller 85 can reduce the average current at a given electrode element 52 based on real-time temperature measurements by turning off the current to the given electrode element 52 and waiting until temperature measured using the temperature sensors 54 drops below a second temperature threshold (e.g., below 38° C.). Once the temperature drops below this second temperature threshold, the controller 85 can restore the current to the given electrode element 52. This may be accomplished, for example, by controlling the state of the control input to the switch 56 that was previously turned off so that the switch 56 reverts to the ON state, which will allow current to flow between the electrical conductor and the respective electrode element 52. In these embodiments, the current to a given electrode element 52 may be repeatedly switched off and on based on real-time temperature measurements in order to keep the temperature at the given electrode element 52 below the safety threshold.

In the FIG. 3 embodiment, each of the transducer assemblies 31, 32 is connected to the AC signal generator 30 via a respective cable. Notably only 4 conductors are required in each of the cables that run between the transducer assembly and the AC signal generator 30 (i.e., Vcc, data, and ground for implementing serial data communication, plus one additional conductor 51 for the AC current TTFields signal).

Note that in FIG. 3, each transducer assembly 31, 32 includes nine electrode elements 52, nine switches 56, and nine temperature sensors 54. But in alternative embodiments, each transducer assembly 31, 32 can include a different number (e.g., between 8 and 25) of electrode elements 52 and a corresponding number of switches and temperature sensors.

Figure 4:
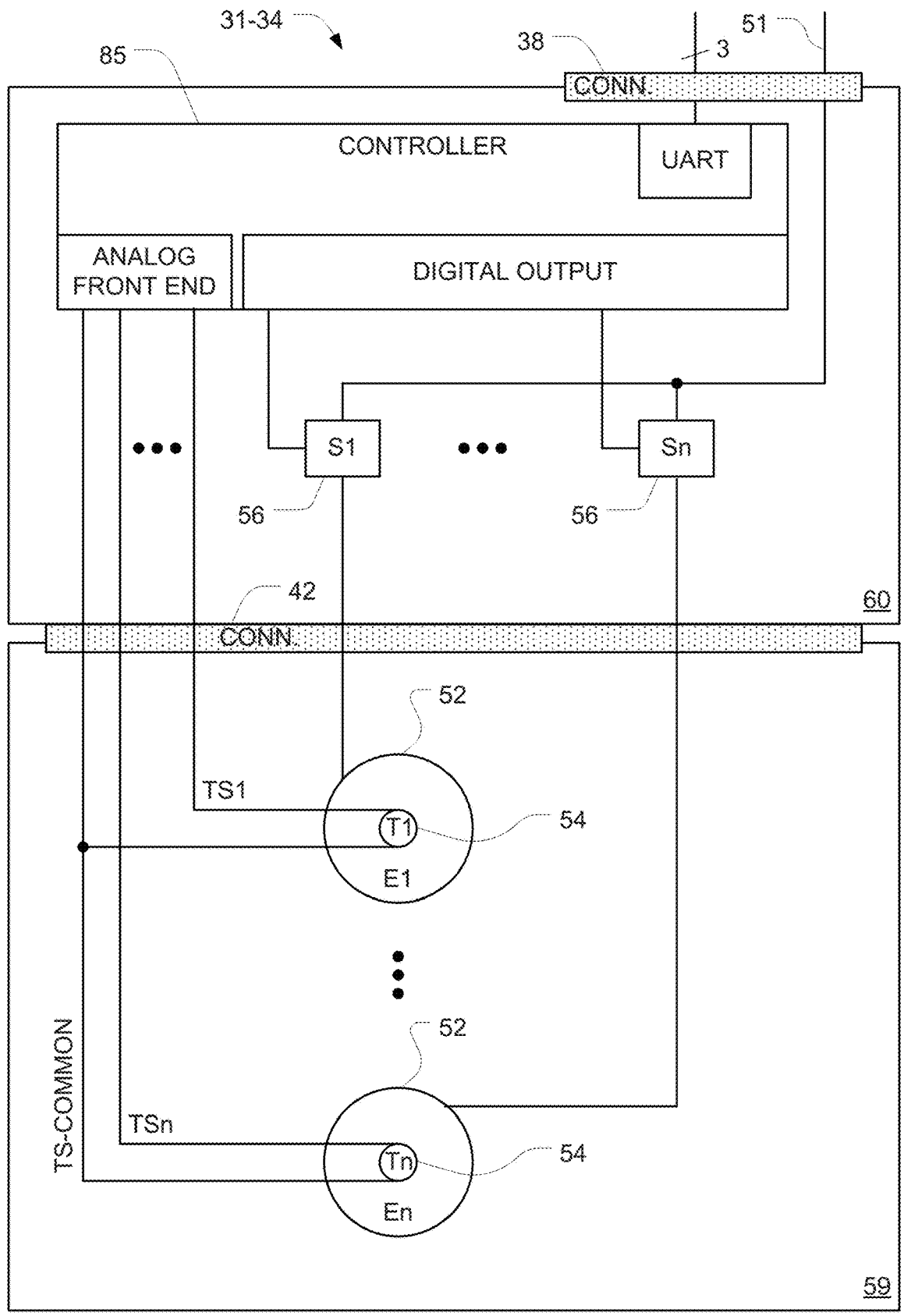
FIG. 4 is a schematic representation of a mechanical layout that may be used for one of the transducer assemblies depicted in FIG. 3.

FIG. 4 is a schematic representation of one mechanical layout that may be used for any given one of the left/right transducer assemblies 31, 32 depicted in FIG. 3, or the front/back transducer assemblies 33, 34 (not shown in FIG. 3) that are connected to the second output OUT2 of the AC signal generator 30 depicted in FIG. 3. In this embodiment, each transducer assembly 31-34 includes a plurality of capacitively coupled electrode elements 52 that are mounted on a support 59. The electrode elements 52 are configured for placement against the subject's body (preferably with a layer of hydrogel disposed on the surface of the electrode elements 52 that face the subject's body), and the support 59 holds the plurality of electrode elements 52 against the subject's body so that the dielectric layer of the electrode elements 52 faces the subject's body. The support 59 is preferably flexible and may be made of a material such as cloth or a dense medical foam. An adhesive layer may be used to affix the support 59 to the person's body. The temperature sensors 54 are positioned so that they can sense the temperature at each of the electrode elements 52. For example, each of the temperature sensors 54 may be positioned adjacent to and/or beneath a corresponding one of the electrode elements 52. In some embodiments, each of the electrode elements 52 has a small hole in its center, and the temperature sensors 54 are positioned in that small hole. Note that although only two electrode elements 52 and corresponding switches 56 and temperature sensors 54 are depicted in FIG. 4, a larger number (e.g., between 9 and 25) of each of those components is preferably used. This is denoted by the nomenclature E1 . . . En, S1 . . . Sn, and T1 . . . Tn in FIG. 3 for the electrode elements, switches, and temperature sensors, respectively.

A module 60 is mounted (either directly or through intervening components) to the support 59. The module 60 includes the controller 85 and the switches 56. Optionally, the module 60 can connect to the support 59 using an electrical connector 42, in which case one half of the connector 42 is provided on the module 60, and the mating half of the connector 42 is provided on the support 59. When both halves of the connector 42 are mated, signals from thermistors 54 will travel through wiring on the support 59 (e.g., flex circuit wiring), through the connector 42, and into the controller 85 on the module 60. In addition, the AC current signal from the output side of each of the switches 56 travels through the connector 42 and through wiring on the support 59 (e.g., flex circuit wiring) to each of the electrode elements 52.

Including the optional connector 42 provides an advantage over embodiments that do not include that connector because the array of electrode elements 52 are preferably sterilized before use. Sterilization is ordinarily performed using either radiation or gas. Since radiation can interfere with electronics, assemblies in which the electronics cannot be disconnected from the array of electrode elements 52 can only be sterilized with gas. On the other hand, if the electronic components 56, 85 can be disconnected from the array of electrode elements 52 via the connector 42 (as it is in FIG. 4), the electronics can be plugged in after sterilization. This permits sterilization of the array of electrode elements 52 to be performed using either gas or radiation without risk of damage to the sensitive electronic components 56, 85.

As noted above, only 4 conductors are required in each of the cables that run between each of the transducer assemblies 31-34 and the AC signal generator 30 (i.e., Vcc, data, and ground for implementing serial data communication, plus one additional conductor 51 for the AC current TTFields signal). In some preferred embodiments, the connection between the transducer assembly 31-34 and the AC signal generator (shown in FIG. 3) is connectorized using, for example, an electrical connector 38.

In the embodiments described above, the decision to adjust the duty cycle or turn off one or more of the switches 56 in a given transducer assembly 31, 32 in order to reduce the average current to one or more of the electrode elements 52 is made locally in each transducer assembly 31, 32 by the controller 85 within that transducer assembly 31, 32. But in alternative embodiments, the decision to adjust the duty cycle or turn off one or more of the switches 56 may be made by the AC signal generator 30 (or another remote device e.g., a central hub disposed between the AC signal generator 30 and each of the transducer assemblies 31, 32). In these embodiments, the controller 85 in each of the transducer assemblies 31, 32 obtains the temperature readings from each of the temperature sensors 54 in the respective transducer assembly and transmits those temperature readings to the AC signal generator 30 via the UART of the controller 85. The AC signal generator 30 decides which, if any, of the switches require a duty cycle adjustment or should be turned off based on the temperature readings that it received, and transmits a corresponding command to the corresponding controller 85 in the corresponding transducer assembly 31, 32. When the controller 85 receives this command from the AC signal generator 30, the controller 85 responds by setting its digital output to a state that will switch off the corresponding switch 56 at the appropriate times, in order to carry out the command that was issued by the AC signal generator 30. In these embodiments, the AC signal generator 30 can also be programmed to reduce its output current if a reduction in current is necessary to keep the temperature at each of the electrode elements 52 below the safety threshold.

In these embodiments, the controller 85 may be programmed to operate as a slave to a master controller located in the AC signal generator 30. In these embodiments, the controller 85 starts out in a quiescent state, where all it does is monitor incoming commands from the master controller that arrive via the UART. Examples of commands that can arrive from the master controller include a "collect temperature data" command, a "send temperature data" command, and a "set switches" command. When the controller 85 recognizes that a "collect temperature data" command has arrived, the controller 85 will obtain temperature readings from each of the temperature sensors 54 and store the result in a buffer. When the controller 85 recognizes that a "send temperature data" command has arrived, the controller 85 will execute a procedure that transmits the previously collected temperature readings from the buffer to the AC signal generator 30 via the UART 86. And when the controller 85 recognizes that a "set switches" command has arrived, the controller 85 will execute a procedure to output appropriate voltages on its digital output in order to set each of the switches 56 to a desired state (i.e., either ON, OFF, or switching between on and off at a commanded duty cycle) based on data that arrives from the AC signal generator 30.

In the embodiments described above, a single controller 85 is used in each of the transducer assemblies 31, 32 to control the switches 56 in that assembly and also to obtain temperature measurements from each of the temperature sensors 54 in that assembly. In alternative embodiments, instead of using a single controller 85 to control the switches 56 and to obtain the temperature measurements, those two tasks may be divided between two controllers, one of which is only used to control the switches 56, and the other of which is used to obtain the temperature measurements from each of the temperature sensors 54 (e.g., using any of the approaches described above). In these embodiments, these two controllers may communicate directly with each other, and/or the AC signal generator 30.

In other alternative embodiments (not shown), temperature measurement does not rely on a local controller that is positioned in the vicinity of the electrode elements 52. Instead, wires run from each of the temperature sensors 54 back to the AC signal generator 30 (or to a central hub disposed between the AC signal generator 30 and each of the transducer assemblies 31, 32), and the AC signal generator uses signals that arrive via these wires to determine the temperature at each of the temperature sensors 54. Note, however, that in these embodiments, the cables that run to the transducer arrays will require a larger number of conductors, which may reduce the flexibility of the cables and increase the cumbersomeness of the cables.

Figure 5:
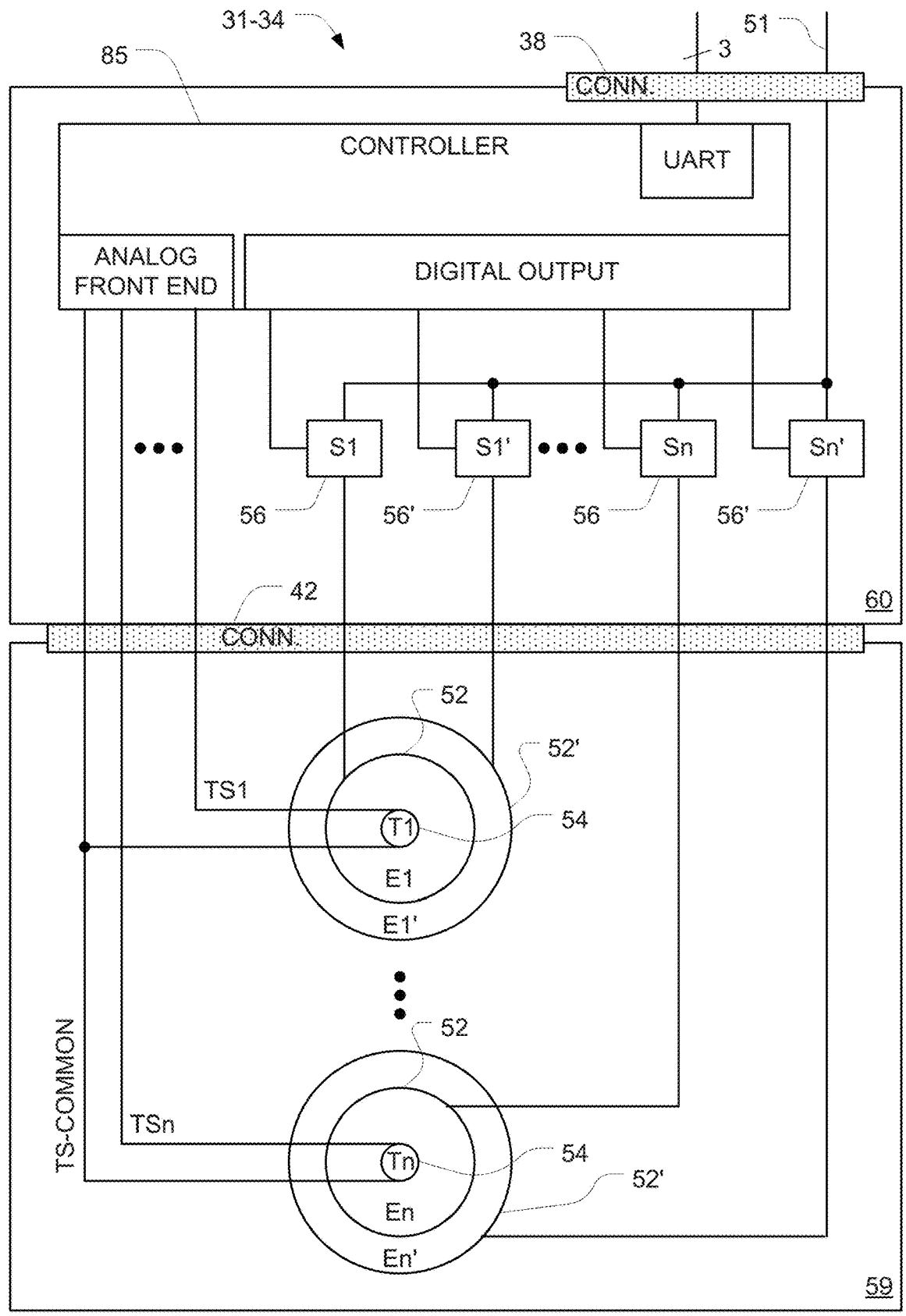
FIG. 5 depicts an alternative configuration that groups the transducer elements into n sets, and uses a single temperature sensor to measure the temperature for each of those n sets.

In the FIGS. 3 and 4 embodiments described above, the number of temperature sensors 54 matches the number of electrode elements 52, and each temperature sensor 54 is dedicated to sensing the temperature at a single one of the electrode elements 52. FIG. 5 depicts an alternative configuration that groups the electrode elements into n sets, and uses a single temperature sensor to measure the temperature for each of these n sets. In some preferred embodiments, n is between 9 and 25.

For this to work, the electrode elements within any given set must be adjacent to each other. In the embodiment illustrated in FIG. 5, each set includes an inner disc-shaped electrode element 52 that is similar to the electrode elements described above in connection with FIG. 4, plus an additional outer ring-shaped electrode element 52' that surrounds the inner disc-shaped electrode element 52 and is concentric thereto. The temperature sensor 54 is positioned in the center of the inner disc-shaped electrode element 52. Each electrode element 52, 52' has its own individual switch 56, 56' that enables the controller 85 to switch the current on or off. In alternative embodiments (not shown) additional concentric ring-shaped electrode elements may be added to each set. In other alternative embodiments (not shown) instead of arranging all of the electrode elements in any given set in concentric rings, the electrode elements in each set may be laid out next to each other (e.g. using electrode elements that are arranged like the slices of a pie, and positioning the temperature sensor in the center of the pie). In these alternative embodiments, each electrode element will have its own individual switch that enables the controller 85 to switch the current on or off individually.

The FIG. 5 embodiment can be operated to achieve the same results described above in connection with FIGS. 3 and 4 by programming the controller 85 to always switch the current to all of the electrode elements 52, 52' in any given set on or off together. But this embodiment also provides additional flexibility. More specifically, if the controller 85 determines, based on a signal from one of the temperature sensors 54, that a hot region exists in a given transducer assembly, the controller in this embodiment has the option to reduce the current at that hot region by deactivating some but not all of the electrode elements that correspond to the hot region. Assume, for example, that the signal from the first temperature sensor 54 (T1) beneath the first set of electrodes 52, 52' (E1/E1') reveals that the temperature beneath that set of electrodes has risen above 40° C. The controller 85 in this FIG. 5 embodiment has the option to reduce the current in that region by issuing a command to turn off only some of the corresponding switches. This could be accomplished, for example by turning off the switch S1 that feeds the inner element E1, and leaving the switch S1' that feeds the outer element E1' on. Alternatively, the same result could also be accomplished by turning off the switch S1' that feeds the outer element E1', and leaving the switch S1 that feeds the inner element E1 on.

Optionally, the duty cycle for each of the individual electrode elements within any given set of electrodes elements in the FIG. 5 embodiment may be adjusted individually to obtain additional control over the average current that is coupled in through any region, as described above in connection with FIGS. 3 and 4.

Note that although only two sets of electrode elements 52, 52' and corresponding switches 56, 56' and temperature sensors 54, 54' are depicted in FIG. 5, a larger number (e.g., between 9 and 25) of sets of those components is preferably used. This is denoted by the nomenclature E1 . . . En, E1' . . . En', S1 . . . Sn, S1' . . . Sn', T1 . . . Tn and T1' . . . Tn' in FIG. 5 for the electrode elements, switches, and temperature sensors, respectively.

Figure 6:
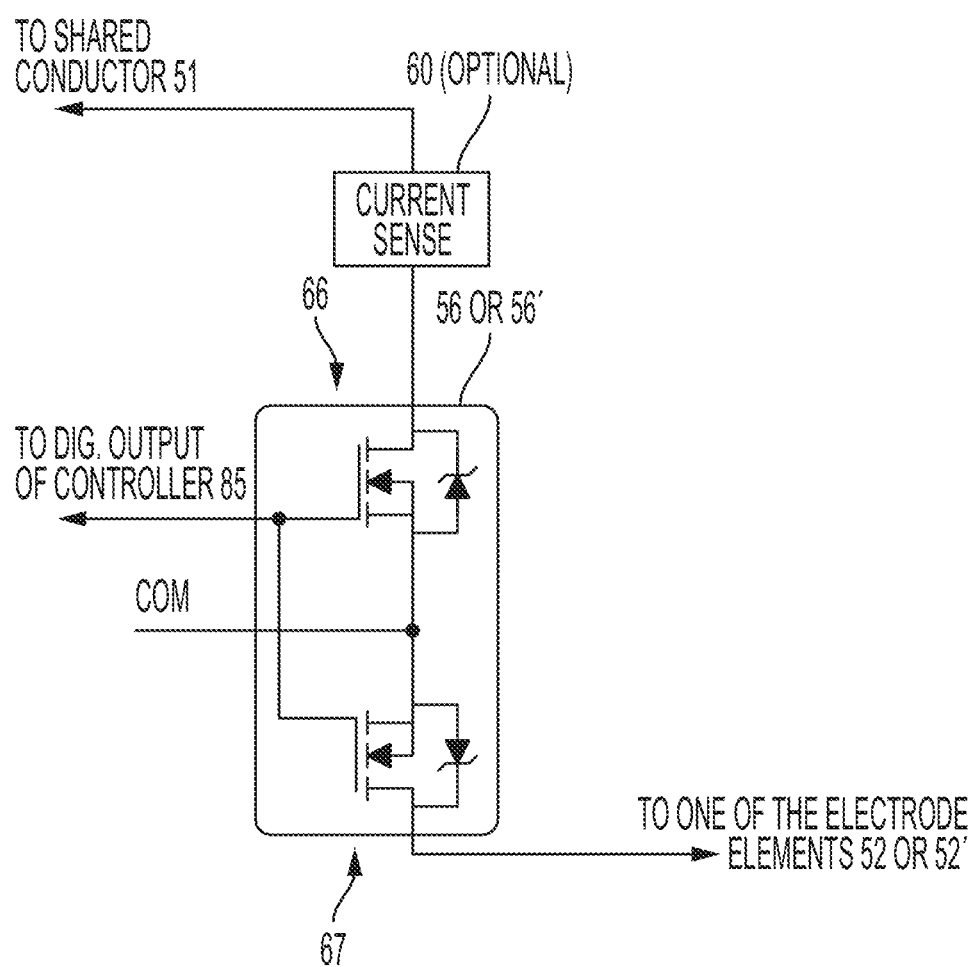
FIG. 6 is a schematic diagram of a circuit that is suitable for implementing the switches in the FIG. 3-5 embodiments.

FIG. 6 is a schematic diagram of a circuit that is suitable for implementing the switches 56, 56' in the FIG. 3-5 embodiments described above. The circuit includes two field effect transistors 66, 67 wired in series, which is a configuration that can pass current in either direction. One example of a suitable FET for this circuit is the BSC320N20NSE. (Note that the diodes depicted in FIG. 6 are inherently included within the FETs 66, 67 themselves.) The series combination of the two FETs 66, 67 will either conduct or block the flow of electricity, depending on the state of the control input that arrives from one of the digital outputs of the controller 85 described above. When the series combination is conducting, current can flow between the shared conductor 51 and the respective electrode element 52, 52'. On the other hand, when the series combination of FETs 66, 67 is not conducting, current will not flow between the shared conductor 51 and the respective electrode element 52, 52'.

Optionally, a current sensing circuit 60 may be positioned in series with the switch 56, 56'. The current sensing circuit 60 may be implemented using any of a variety of conventional approaches that will be apparent to persons skilled in the relevant arts. When the current sensing circuit 60 is included, it generates an output that is representative of the current, and this output is reported back to the controller 85 (shown in FIGS. 3-5). The controller 85 can then use this information to determine whether the measured current is as expected and take appropriate action if necessary. For example, if an overcurrent condition is detected, the controller 85 can turn off the corresponding switch. Of course, in those embodiments where the current sensing circuit 60 is omitted, it should be replaced with the wire (or other conductor) so that the current can flow between the shared conductor 51 and the top leg of the upper FET 60.

In the illustrated embodiment, the current sensing circuit 60 is positioned between the shared conductor 51 and the top leg of the upper FET 60. But in alternative embodiments, the current sensing circuit may be positioned between the bottom leg of the lower FET 67 and the respective electrode element 52, 52'. And in other alternative embodiments (not shown), the current sensing circuit may be integrated within the circuitry of the switch itself.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an alternating electric field to a subject's body, the apparatus comprising:
   a plurality of capacitively coupled electrode elements, each of the electrode elements having a dielectric layer;
   a support configured to hold the plurality of electrode elements against the subject's body with the dielectric layer of the electrode elements facing the subject's body;
   a plurality of temperature sensors, wherein each of the temperature sensors is positioned to sense a temperature at a respective electrode element and generate a respective signal indicative of the sensed temperature;
   an electrical conductor;
   a plurality of electrically controlled switches, wherein each of the switches is configured to, depending on a state of a respective control input, either (a) allow current to flow between the electrical conductor and a respective electrode element or (b) prevent current from flowing between the electrical conductor and the respective electrode element; and
   a controller configured to control the state of the control input of each of the switches.

2. The apparatus of claim 1, wherein the controller is further configured to
   accept, from each of the temperature sensors, the respective signal indicative of the sensed temperature,
   determine, based on the accepted signals, a duty cycle at which a given electrode element should be driven, and
   periodically toggle the state of the control input of a switch that corresponds to the given electrode element at the determined duty cycle in order to periodically prevent current from flowing between the electrical conductor and the given electrode element.

3. The apparatus of claim 1, wherein the controller is further configured to
   accept, from each of the temperature sensors, the respective signal indicative of the sensed temperature,
   determine, based on the accepted signals, whether a temperature at each of the electrode elements exceeds an upper threshold, and if it has been determined that a temperature at a given electrode element exceeds the upper threshold, control the state of the control input of the respective switch to prevent current from flowing between the electrical conductor and the given electrode element.

4. The apparatus of claim 3, wherein the controller is further configured to, after controlling the state of the control input to a given switch to prevent current from flowing between the electrical conductor and a respective electrode element, determine, based on the accepted signal from the respective temperature sensor whether a temperature at the respective electrode element has dropped below a lower threshold, and subsequently control the state of the control input to the given switch to allow current to flow between the electrical conductor and the respective electrode element.

5. The apparatus of claim 1, wherein the controller is further configured to
accept the signal from each of the temperature sensors, and
control the state of the control inputs of the plurality of switches based on the signal from each of the temperature sensors.

6. The apparatus of claim 1, wherein the plurality of capacitively coupled electrode elements comprises at least 9 capacitively coupled electrode elements.

7. The apparatus of claim 1, wherein each of the capacitively coupled electrode elements comprises a conductive plate with a flat face, and wherein the dielectric layer is disposed on the flat face of the conductive plate.

8. The apparatus of claim 1, wherein the electrical conductor comprises a trace on a flex circuit.

9. The apparatus of claim 1, wherein the plurality of electrically controlled switches and the controller are positioned on a module that is attached to the support via a multi-conductor connector.

10. The apparatus of claim 1, wherein
the plurality of capacitively coupled electrode elements is a plurality of capacitively coupled sets of at least two electrode elements, each of the electrode elements having a dielectric layer;
the support configured to hold the plurality of electrode elements is a support configured to hold the plurality of sets of electrode elements against the subject's body with the dielectric layer of the electrode elements facing the subject's body; and
each of the plurality of temperature sensors is positioned to sense a temperature at a respective set of electrode elements and generate a respective signal indicative of the sensed temperature.

11. The apparatus of claim 10, wherein all of the electrode elements within any given set of electrode elements are arranged concentrically.

12. The apparatus of claim 10, wherein the controller is further configured to
accept, from each of the temperature sensors, the respective signal indicative of the sensed temperature,
determine, based on the accepted signals, a duty cycle at which a given electrode element should be driven, and
periodically toggle the state of the control input of a switch that corresponds to the given electrode element at the determined duty cycle in order to periodically prevent current from flowing between the electrical conductor and the given electrode element.

13. The apparatus of claim 10, wherein the controller is further configured to
accept, from each of the temperature sensors, the respective signal indicative of the sensed temperature,
determine, based on the accepted signals, whether a temperature at each set of electrode elements exceeds an upper threshold, and
if it has been determined that a temperature at a given set of electrode elements exceeds the upper threshold, control the state of the control input of at least one respective switch to prevent current from flowing between the electrical conductor and at least one of the electrode elements in the given set of electrode elements.

14. The apparatus of claim 10, wherein the controller is further configured to
accept the signal from each of the temperature sensors,
transmit data describing the temperature at each of the temperature sensors to a second controller,
receive data from the second controller indicating which of the switches should be turned off, and
control the state of the control inputs of the plurality of switches based on the data received from the second controller.

15. The apparatus of claim 10, wherein the plurality of electrically controlled switches and the controller are positioned on a module that is attached to the support via a multi-conductor connector.

16. An apparatus for applying an alternating electric field to a subject's body, the apparatus comprising:
a plurality of first electrode elements;
a support configured to hold the plurality of first electrode elements against a subject's body;
a plurality of temperature sensors, wherein each of the temperature sensors is positioned to sense a temperature at a respective first electrode element and generate a respective signal indicative of the sensed temperature;
an electrical conductor;
a plurality of electrically controlled first switches, wherein each of the first switches is wired in series with a respective first electrode element in a circuit that begins at the electrical conductor and ends at the respective first electrode element, and wherein each of the first switches is configured to switch on or off independently of other first switches based on a state of a respective control input; and
a controller configured to generate an output that determines the state of the control input for each of the first switches.

17. The apparatus of claim 16, wherein each of the first electrode elements comprises a capacitively coupled electrode element having a dielectric layer, and
wherein the support is configured to hold the plurality of first electrode elements against a subject's body with the dielectric layer of the plurality of first electrode elements facing the subject's body.

18. The apparatus of claim 16, further comprising:
a plurality of second electrode elements, wherein each of the second electrode elements is positioned adjacent to a respective first electrode element; and
a plurality of electrically controlled second switches, wherein each of the second switches is wired in series with a respective second electrode element in a circuit that begins at the electrical conductor and ends at the respective second electrode element, and wherein each of the second switches is configured to switch on or off independently of other second switches based on a state of a respective control input, wherein the support is configured to hold the plurality of second electrode elements against the subject's body, and wherein the controller is further configured to generate an output that determines the state of the control input for each of the second switches.

19. The apparatus of claim 18, wherein each of the first electrode elements comprises a capacitively coupled electrode element having a dielectric layer, and each of the second electrode elements comprises a capacitively coupled electrode element having a dielectric layer, and wherein the support is configured to (a) hold the plurality of first electrode elements against a subject's body with the dielectric layer of the first electrode elements facing the subject's body, and (b) hold the plurality of second electrode elements against a subject's body with the dielectric layer of the second electrode elements facing the subject's body.

20. The apparatus of claim 18, wherein each of the second electrode elements is concentric with the adjacent respective first electrode element.

\* \* \* \* \*